(12) United States Patent
Grigorian et al.

(10) Patent No.: US 10,117,681 B2
(45) Date of Patent: Nov. 6, 2018

(54) DISTRACTION PLATE SYSTEM

(71) Applicant: IMPLANTABLE DESIGN, LLC, Nashville, TN (US)

(72) Inventors: Arthur A. Grigorian, Atlanta, GA (US); Leonid S. Tadevosyan, Fort Lee, NJ (US); Arthur John Ulm, III, Nashville, TN (US)

(73) Assignee: IMPLANTABLE DESIGN, LLC, Nashville, TN (US)

( * ) Notice: Subject to any disclaimer, the term of this patent is extended or adjusted under 35 U.S.C. 154(b) by 0 days.

(21) Appl. No.: 15/517,250

(22) PCT Filed: Oct. 6, 2015

(86) PCT No.: PCT/US2015/054246
§ 371 (c)(1),
(2) Date: Apr. 6, 2017

(87) PCT Pub. No.: WO2016/057514
PCT Pub. Date: Apr. 14, 2016

(65) Prior Publication Data
US 2017/0245901 A1    Aug. 31, 2017

Related U.S. Application Data (60) Provisional application No. 62/060,298, filed on Oct. 6, 2014, provisional application No. 62/104,706, filed on Jan. 17, 2015.

(51) Int. Cl.
| | | |
|---|---|---|
| *A61B 17/80* | (2006.01) | |
| *A61B 17/70* | (2006.01) | |
| *A61B 17/56* | (2006.01) | |

(52) U.S. Cl.
CPC ...... *A61B 17/7059* (2013.01); *A61B 17/7082* (2013.01); *A61B 17/8014* (2013.01);
(Continued)

(58) Field of Classification Search
CPC ............. A61B 17/8033–17/8047; A61B 17/80
See application file for complete search history.

(56) References Cited

U.S. PATENT DOCUMENTS

| | | | |
|---|---|---|---|
| 4,911,593 A | 3/1990 | Kephart | |
| 5,275,601 A * | 1/1994 | Gogolewski | ....... A61B 17/8052 411/399 |

(Continued)

FOREIGN PATENT DOCUMENTS

WO    2009153486 A1    12/2009

OTHER PUBLICATIONS

Fransen, Patrick, "A Simplified Technique for Anterior Cervical Discectomy and Fusion Using a Screw-Plate Implanted Over the Caspar Distractor Pins", Acta Orthopaedica Belgica, 2010, No. 4, pp. 546-548, vol. 76/4, (From the Clinique du Parc Leopold, Brussels, Belgium), http://www.actaorthopaedica.be/, official journal of the Belgian Society of Orthopaedics and Traumatology, at http://www.actaorthopaedica.be/acta/article.asp?lang=en&navid=243&id=14899&mod=acta.

(Continued)

*Primary Examiner* — Eduardo C Robert
*Assistant Examiner* — Michelle C Eckman
(74) *Attorney, Agent, or Firm* — Shane V. Cortesi (57) ABSTRACT

The present invention provides plate systems for distracting and fixating vertebral bodies of animal (preferably human) spines. In some embodiments, the system includes: a biocompatible plate with at least two holes, at least two biocompatible distraction screws for insertion through the holes, each screw having an expandable head, a bore and a threaded shank, and at least two biocompatible fixating screws with threaded shanks. Insertion of the fixating screws into the distraction screws causes the expandable heads to expand and lock to the biocompatible plate. Optionally, the (Continued)

plate and the expandable heads comprises mating teeth configured to lock the expandable heads to the plate upon expansion of the expandable heads. The present invention also relates to use of the plate system to distract and fixate vertebral bodies.

23 Claims, 9 Drawing Sheets

(52) U.S. Cl.
CPC ...... *A61B 17/8038* (2013.01); *A61B 17/8052* (2013.01); *A61B 2017/564* (2013.01)

(56) References Cited

U.S. PATENT DOCUMENTS

| | | | | |
|---|---|---|---|---|
| 6,117,173 | A * | 9/2000 | Taddia | A61B 17/86 606/104 |
| 6,235,033 | B1 * | 5/2001 | Brace | A61B 17/8038 606/288 |
| 6,306,136 | B1 * | 10/2001 | Baccelli | A61B 17/7059 606/279 |
| 6,440,136 | B1 | 8/2002 | Gambale et al. | |
| 6,565,573 | B1 | 5/2003 | Ferrante et al. | |
| 6,575,975 | B2 | 6/2003 | Brace et al. | |
| 6,613,053 | B1 * | 9/2003 | Collins | A61B 17/7059 606/289 |
| 6,620,167 | B2 | 9/2003 | Deslauriers et al. | |
| D480,618 | S | 10/2003 | Petrsorich | |
| 6,890,334 | B2 | 5/2005 | Brace et al. | |
| 6,988,432 | B2 | 1/2006 | Brooks | |
| 7,052,499 | B2 * | 5/2006 | Steger | A61B 17/8047 606/280 |
| 7,063,701 | B2 * | 6/2006 | Michelson | A61B 17/8605 606/307 |
| 7,229,442 | B2 * | 6/2007 | Schafer | A61B 17/8052 606/272 |
| 7,476,228 | B2 | 1/2009 | Abdou | |
| 7,766,948 | B1 * | 8/2010 | Leung | A61B 17/8014 606/291 |
| 7,824,428 | B2 | 11/2010 | Mikkonen et al. | |
| 7,988,714 | B2 * | 8/2011 | Puekert | A61B 17/8038 606/280 |
| 8,388,666 | B2 * | 3/2013 | Castaneda | A61B 17/8047 606/290 |
| 8,500,748 | B2 | 8/2013 | Yu | |
| 8,500,782 | B2 * | 8/2013 | Kovach | A61B 17/7059 606/280 |
| 8,506,607 | B2 * | 8/2013 | Eckhof | A61B 17/8057 606/286 |
| 8,652,183 | B1 * | 2/2014 | Truman | A61B 17/8038 606/281 |
| 8,668,419 | B2 | 3/2014 | Hardt et al. | |
| 9,155,577 | B2 * | 10/2015 | Pfefferle | A61B 17/8052 |
| 9,351,774 | B2 | 5/2016 | Konieczynski et al. | |
| 9,468,481 | B2 * | 10/2016 | Klein | A61B 17/8605 |
| 9,763,715 | B2 * | 9/2017 | Mather | A61B 17/8052 |
| 9,924,984 | B2 * | 3/2018 | Hartdegen | A61B 17/7233 |
| 2002/0110437 | A1 | 8/2002 | Kirimoto | F16B 23/0061 411/119 |
| 2003/0171753 | A1 | 9/2003 | Collins et al. | |
| 2004/0030336 | A1 * | 2/2004 | Khanna | A61B 17/8038 606/86 B |
| 2004/0127896 | A1 * | 7/2004 | Lombardo | A61B 17/8042 606/290 |
| 2005/0096657 | A1 * | 5/2005 | Autericque | A61B 17/7059 623/17.11 |
| 2005/0165400 | A1 * | 7/2005 | Fernandez | A61B 17/8047 606/281 |
| 2005/0273105 | A1 * | 12/2005 | Konieczynski | A61B 17/7059 606/289 |
| 2006/0122602 | A1 * | 6/2006 | Konieczynski | A61B 17/7059 606/281 |
| 2006/0122604 | A1 * | 6/2006 | Gorhan | A61B 17/8038 606/86 B |
| 2006/0142766 | A1 | 6/2006 | Schafer | |
| 2006/0264936 | A1 * | 11/2006 | Partin | A61B 17/683 606/281 |
| 2007/0225717 | A1 * | 9/2007 | Hawkes | A61B 17/7059 606/279 |
| 2008/0004627 | A1 | 1/2008 | Dalton | |
| 2008/0193898 | A1 | 8/2008 | Forster | |
| 2008/0234677 | A1 | 9/2008 | Dahners et al. | |
| 2009/0012571 | A1 * | 1/2009 | Perrow | A61B 17/1671 606/280 |
| 2009/0192553 | A1 * | 7/2009 | Maguire | A61B 17/8038 606/305 |
| 2009/0264934 | A1 | 10/2009 | Youssef | |
| 2009/0270927 | A1 * | 10/2009 | Perrow | A61B 17/7059 606/286 |
| 2009/0312803 | A1 * | 12/2009 | Austin | A61B 17/8014 606/305 |
| 2010/0211116 | A1 * | 8/2010 | Suh | A61B 17/8033 606/305 |
| 2010/0222827 | A1 | 9/2010 | Griffiths et al. | |
| 2010/0312280 | A1 * | 12/2010 | Overes | A61B 17/68 606/264 |
| 2011/0071575 | A1 | 3/2011 | Bhatnagar et al. | |
| 2011/0270326 | A1 * | 11/2011 | Black | A61B 17/8038 606/308 |
| 2012/0179207 | A1 * | 7/2012 | Mekhail | A61B 17/7059 606/281 |
| 2012/0253407 | A1 * | 10/2012 | Dunn | A61B 17/8076 606/289 |
| 2012/0303071 | A1 * | 11/2012 | Black | A61B 17/8047 606/305 |
| 2013/0125714 | A1 | 5/2013 | Dahners | |
| 2013/0190825 | A1 * | 7/2013 | Perrow | A61B 17/8042 606/281 |
| 2013/0282065 | A1 | 10/2013 | Gorhan et al. | |
| 2014/0249587 | A1 * | 9/2014 | Cawley | A61B 17/7059 606/291 |
| 2014/0296925 | A1 * | 10/2014 | Lawson | A61B 17/8033 606/289 |
| 2015/0100089 | A1 * | 4/2015 | Richelsoph | A61B 17/7001 606/246 |
| 2015/0216573 | A1 * | 8/2015 | Chin | A61B 17/8052 606/279 |
| 2015/0230841 | A1 | 8/2015 | Freese | |
| 2016/0089191 | A1 * | 3/2016 | Pak | A61B 17/8047 606/291 |
| 2017/0065312 | A1 * | 3/2017 | Lauf | A61B 17/8047 |
| 2017/0245901 | A1 * | 8/2017 | Grigorian | A61B 17/7059 |
| 2017/0333098 | A1 * | 11/2017 | Vasta | A61B 17/8047 |
| 2018/0064478 | A1 * | 3/2018 | Black | A61B 17/8033 |
| 2018/0078296 | A1 * | 3/2018 | Hulliger | A61B 17/8047 |

OTHER PUBLICATIONS

International Search Report from counterpart international application, PCT/US15/54246.

Supplementary European Search Report in corresponding European Patent Application No. EP 15 84 8477, dated May 30, 2018, 9 pp.

* cited by examiner

DISTRACTION PLATE SYSTEM

BACKGROUND

Technical Field

The present invention relates to plate systems for use in fixing vertebral bodies.

Background of the Invention

Removing a herniated disc is a common spinal procedure. The procedure involves placing large temporary bone screws, called distraction screws, into the vertebral bodies directly above and below the diseased disc space in the spine. Once inserted, the surgeon uses the distraction screws to realign the vertebral bodies into the desired anatomical relationship and to temporarily distract the vertebral bodies (or more them apart) so as to permit work within the intervening disc space. The herniated disc is removed and natural or synthetic bone graft material is placed into the evacuated space. The temporary distraction screws are then removed from the vertebral bodies. Next, the surgeon secures a plate to the vertebral bodies to maintain their position using two implantable bones screws, which are screwed into the vertebral bodies.

Removal of the temporary distraction screws is problematic for a number of reasons. First, removal from the vertebral bodies usually produces significant bleeding. Second, the empty distraction holes act as stress concentration points within the vertebral bodies, increasing the likelihood of fracture. Third, the empty holes often interfere with proper placement of the implantable screws and the associated plate. Finally, if another surgery on an adjacent area later becomes necessary, the surgery will require re-dissection through the scarred operative field of the initial procedure, significantly increasing the operative risk of the second procedure for the patient.

There have been prior attempts to address some of the issues associated with removal of distraction screws. For example, U.S. Pat. No. 7,476,228 ("the '228") describes a polyaxial locking screw assembly, in which the distraction screws are also used to secure the plate to the vertebral body. Although the system of the '228 patent eliminates the need for separate distraction and plate screws, the screws may allow the vertebral bodies to move too much. This is obviously problematic, as the principal purpose of the plate is to fix the vertebral bodies into place.

BRIEF SUMMARY

The present disclosure provides plate system for distracting and fixating vertebral bodies comprising:

a) a biocompatible plate comprising a top surface, a bottom surface configured to confront a vertebral body and at least two generally circular holes, each hole comprising a length extending from the top surface to the bottom surface, a diameter, a circumference, and a plurality of teeth spaced evenly about the circumference;

b) at least two biocompatible distraction screws, each biocompatible distraction screw comprising an expandable head, the expandable head generally circular in shape and comprising a circumference, a diameter and a plurality of teeth spaced evenly about the circumference and configured to engage the teeth of one of the generally circular holes, a shank comprising threads located on an exterior surface of the shank a length extending from the head to the shank, and a generally circular bore comprising a top end located in the head, a bottom end located in the shank, and threads spaced about the generally circular bore (which may extend from the top end to the bottom end of the generally circular bore); and c) at least two biocompatible fixating screws, each biocompatible fixating screw comprising a head and a shank comprising threads located on an exterior surface of the shank, each shank of each biocompatible fixating screw configured to be received in one of the generally circular bores and mate with the threads of the bore.

wherein the expandable heads have a radially collapsed state in which the circumferences of the expandable heads are less than the circumferences of the generally circular holes and the diameters of the expandable heads are less than the diameters of the generally circular holes, wherein the expandable heads have a radially expanded state in which the circumferences of the expandable heads are substantially equal to the circumferences of the generally circular holes and the diameters of the expandable heads are substantially equal to the diameters of the generally circular holes, and further wherein insertion of the fixating screws into the distraction screws causes the heads of the distraction screws to move from the radially collapsed state to the radially expanded state.

Optionally, the teeth of the plate holes are adjacent to the plate top surface. Optionally, the teeth of the plate holes are below the plate top surface. Optionally, each generally circular bore tapers in diameter from the bore top end to the bore bottom end. Optionally, each generally circular hole of the plate decreases in diameter and circumference from the plate top surface to the plate bottom surface. Optionally, each generally circular bore comprises a height extending from the bore top end to the bore bottom end and further wherein the threads of each generally circular bore extend substantially along the bore height. Optionally, the heads of the fixating screws are substantially co-planar with the heads of the distraction screws and the top surface of the plate after screwing the fixating screws into the distraction screws. Optionally, the fixating screws are located in the generally circular bores and the distraction screw heads are in the radially expanded state. Optionally, the fixating screws are located in the generally circular bores and the heads of the fixating screws are substantially co-planar with the heads of the distraction screws and below the top surface of the plate. Optionally, the lengths of the distraction screws are greater than the lengths of the generally circular holes so that the heads of the distraction screw heads are co-planar with the top surface of the plate after insertion of the distraction screws into the vertebral bodies. Optionally, one distraction screw shank is located in a vertebral body of an animal (e.g., a human), the other distraction screw shank is located in another (i.e., a different) vertebral body of the animal, and the beads of the distraction screws are in the radially expanded state. Optionally, the vertebral bodies are fixed relative to the plate upon screwing the fixating screws into the distraction screws. Optionally, each distraction screw is positioned in one of the generally circular holes, and each fixating screw is positioned in the bore of one of the distraction screws. Optionally, each expandable head comprises a plurality of grooves. Optionally, the plurality of grooves traverse the expandable head. Optionally, the plurality of grooves on each distraction screw extend into the shank of the distraction screw. Optionally, each generally circular bore is located in the center of an expandable head when the expandable head is in the radially expanded state.

Optionally, the system further comprises at least two screw drivers, each screw driver comprising a top end comprising a handle and a threaded bottom end configured to mate with the threads of a generally circular bore of one of the distraction screws. Optionally, each generally circular bore of each biocompatible distraction screw further comprises a circumference and each head of each biocompatible distraction screw further comprises a circumferential groove extending about the circumference. Optionally, the system further comprises at least two screw drivers, each screw driver comprising a top end comprising a handle, a bottom end, and a flange configured to mate with a circumferential groove of a biocompatible distraction screw.

The present invention also provides a method of fixating a plurality of vertebral bodies (that are preferably located in a human or other animal being operated on). In some embodiments, the method includes:
 a) providing the plate system;
 b) using the screw drivers to drive each distraction screw into a vertebral body by placing the bottom end of each screw driver into a distraction screw (preferably into the generally circular bore of the distraction screw) and rotating the handle of the screw driver (i.e., screwing the distraction screws into the vertebral bodies);
 c) placing the plate over/onto the vertebral bodies such that each distraction screw is located in a generally circular hole;
 d) removing the screw drivers from the generally circular bores; and
 e) radially expanding the expandable heads and fixating the plate to the vertebral bodies by inserting the fixating screws into the generally circular bores and rotating the fixating screws relative to the distraction screws screwing the fixating screws into the distraction screw bores).

Optionally, the method further includes using the screw drivers to distract the vertebral bodies (i.e., increase the distance between the vertebral bodies) prior to step d). Optionally, the method further includes adding bone graft material between the vertebral bodies after distracting the vertebral bodies.

In other embodiments, the plate system includes:
 a) a biocompatible plate comprising a top surface, a bottom surface configured to confront a vertebral body and at least two generally circular holes, each hole comprising a length extending from the top surface to the bottom surface, a diameter, and a circumference;
 b) at least two biocompatible distraction screws, each biocompatible distraction screw comprising an expandable head, the expandable head generally circular in shape and comprising a circumference, a diameter and a plurality of grooves traversing the expandable head, a shank comprising threads located on an exterior surface of the shank, a length extending from the head to the shank, and a generally circular bore comprising a top end located in the head, a bottom end located in the shank, and threads spaced about the generally circular bore (which may extend from the top end to the bottom end of the generally circular bore) and
 c) at least two biocompatible fixating screws, each biocompatible fixating screw comprising a head and a shank comprising threads located on an exterior surface of the shank, each shank of each biocompatible fixating screw configured to be received in a generally circular bore and mate with the threads of the generally circular bore,
wherein the expandable heads have a radially collapsed state in which the circumferences of the expandable heads are less than the circumferences of the generally circular holes and the diameters of the expandable heads are less than the diameters of the generally circular holes,
wherein the expandable heads have a radially expanded state in which the circumferences of the expandable heads are substantially equal to the circumferences of the generally circular holes and the diameters of the expandable heads are substantially equal to the diameters of the generally circular holes, and
further wherein insertion of the fixating screws into the distraction screws causes the distraction screw heads to move from the radially collapsed state to the radially expanded state.

Optionally, each generally circular bore tapers in diameter from the bore top end to the bore bottom end. Optionally, each generally circular hole of the plate decreases in diameter and circumference from the plate top surface to the plate bottom surface. Optionally, each generally circular bore comprises a height extending from the bore top end to the bore bottom end and the threads of each generally circular bore extend substantially along the bore height. Optionally, the heads of the fixating screws are substantially co-planar with the heads of the distraction screws and the top surface of the plate after screwing the fixating screws into the distraction screws. Optionally, the fixating screws are located in the generally circular bores and the distraction screw heads are in the radially expanded state. Optionally, the fixating screws are located in the generally circular bores and the heads of the fixating screws are substantially co-planar with the heads of the distraction screws and below the top surface of the plate. Optionally, the lengths of the distraction screws are greater than the lengths of the generally circular holes so that the distraction screws are co-planar with the top surface of the plate after insertion of the distraction screws into the vertebral bodies. Optionally, one distraction screw shank is located in a vertebral body of an animal, the other distraction screw shank is located in another neighboring vertebral body of the animal, and the heads of the distraction screws are in the radially expanded state. Optionally, the vertebral bodies are fixed relative to the plate upon screwing the fixating screws into the distraction screws. Optionally, each distraction screw is positioned in one of the generally circular holes, and each fixating screw is positioned in the generally circular bore of one of the distraction screws. Optionally, each generally circular bore is located in the center of an expandable head when the expandable head is in the radially expanded state. Optionally, the system further comprises at least two screw drivers, each screw driver comprising a top end comprising a handle, a bottom end, and a flange configured to mate with a circumferential groove of a biocompatible distraction screw. Optionally, the plurality of grooves on each distraction screw extend into the shank of the distraction screw. Optionally, the bottoms of each screw driver comprises threads configured to mate with the threads of a bore of one of the distraction screws. Optionally, the system further comprises at least two screw drivers, each screw driver comprising a top end comprising a handle and a threaded bottom end configured to mate with the threads of a generally circular bore of one of the distraction screws.

The present invention also provides a method of fixating a plurality of vertebral bodies (that are preferably located in a human or other animal being operated on). In some embodiments, the method includes;
 a) providing the plate system;
 b) using the screw drivers to drive each distraction screw into a different vertebral body by placing the bottom end of each screw driver into a distraction screw (preferably into the generally circular bore of the distraction screw) and rotating the handle of the screw driver (i.e., screwing the distraction screws into the vertebral bodies);

c) placing the plate over/onto the vertebral bodies such that each distraction screw is located in a generally circular hole;

d) removing the screw drivers from the generally circular bores; and e) radially expanding the expandable heads and fixating the plate to the vertebral bodies by inserting the fixating screws into the generally circular bores and rotating the fixating screws relative to the distraction screws screwing the fixating screws into the distraction screw bores).

Optionally, the method further includes using the screw drivers to distract the vertebral bodies (i.e., increase the distance between the vertebral bodies) prior to step d). Optionally, the method further includes adding bone graft material between the vertebral bodies after distracting the vertebral bodies.

BRIEF DESCRIPTION OF THE DRAWINGS

FIG. 14 illustrates a side, cross-sectional view of the plate system of FIG. 13 that further includes two fixating screws; in FIG. 14 up arrows illustrate that the screw drivers are moved upwards, and then the screw drivers are moved downwards and used to drive fixating screws into the distraction screws.

FIG. 16 illustrates a top, perspective view of a distraction screw and plate of another embodiment of the present invention; in FIG. 16, the distraction screw head and plate comprise mating threads that, upon expansion of the distraction screw head, lock the distraction screw into place.

FIG. 20 illustrates a close-up, top, plan view of the plate and distraction screw of FIG. 16; in FIG. 20, the expandable head of the distraction screw is in the radially collapsed state.

FIG. 21 illustrates a close-up, top, plan view of the plate and distraction screw of FIG. 16; in FIG. 21, the expandable head of the distraction screw is in the radially collapsed state and the distraction screw is rotated relative to the plate, as compared to FIG. 20

FIG. 22 also illustrates a close-up, top, plan view of the plate and distraction screw of FIG. 16; in FIG. 22, the expandable head of the distraction screw is in the radially collapsed state.

FIG. 23 illustrates a close-up, top, plan view of the plate and distraction screw of FIG. 16; in FIG. 23, the expandable head of the distraction screw is in the radially expanded state.

DETAILED DESCRIPTION

With reference to FIGS. 1-23 the present disclosure provides a plate system, generally designated by the numeral 10 for distracting and fixating vertebral bodies 11. In the drawings, not all reference numbers are included in each drawing for the sake of clarity. Generally, as described in greater detail below, the system 10 includes: a biocompatible plate 12 with at least two holes 15, at least two biocompatible distraction screws 20 for insertion through the holes 15, each distraction screw 20 having an expandable head 21, a bore 27 and a threaded shank 25, and at least two biocompatible fixating screws 31 with threaded shanks 33. Insertion of the fixating screws 31 into the distraction screws 20 causes the expandable heads 21 to expand and lock to the biocompatible plate 12. Optionally, the plate 12 and the expandable heads 21 comprise mating teeth 19 and 24 configured to lock the expandable heads 21 to the plate 12 upon expansion of the expandable heads 21, as illustrated in FIGS. 16-23. The present invention also relates to use of the plate system 10 to distract and fixate vertebral bodies 11. It will be understood that the plate system 10 can include three or more holes 15 and three or more biocompatible distraction screws 20 if, for example, the surgeon desires to fixate three or more vertebral bodies 11. It will be appreciated that the plate system 10 may be used in any suitable region in the spine, including for example, the cervical, thoracic and lumbar levels.

Figures 1, 2, 3, 4:
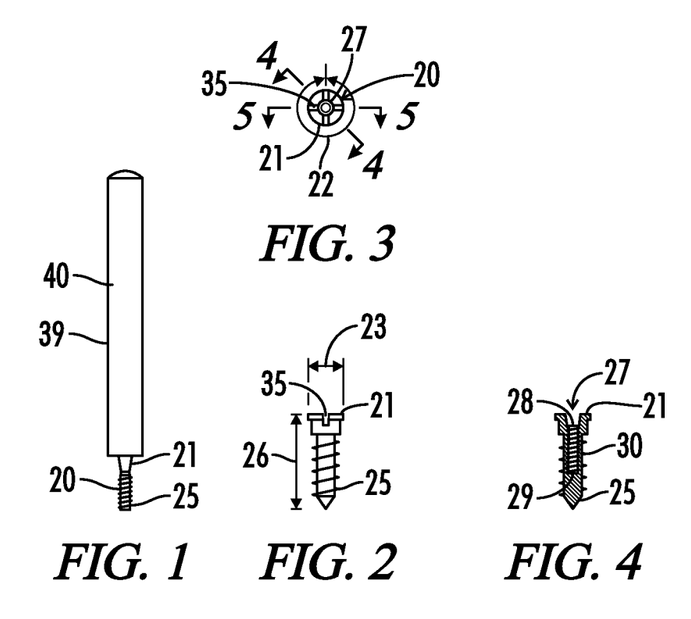
FIG. 1 illustrates a side, elevation view of one embodiment of a screw driver and distraction screw for use with the plate systems of the present invention.
FIG. 2 illustrates a side, elevation view of one embodiment of a distraction screw with an expandable head for use with the plate systems of the present invention.
FIG. 3 illustrates a top, plan view of the distraction screw of FIG. 2.
FIG. 4 illustrates a side, cross-sectional view of the distraction screw of FIG. 3, taken along line 4-4 of FIG. 3.
Figure 5:
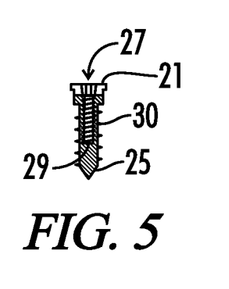
FIG. 5 illustrates a side, cross-sectional view of the distraction screw of FIG. 3, taken along line 5-5 of FIG. 3.
Figure 6:
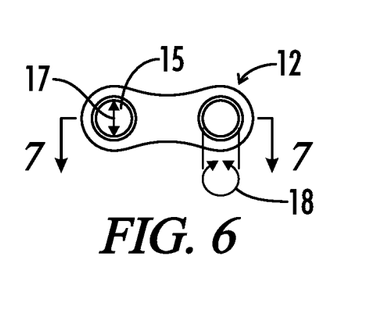
FIG. 6 illustrates a top plan view of one embodiment of a plate for use with the plate systems of the present invention.
Figure 7:
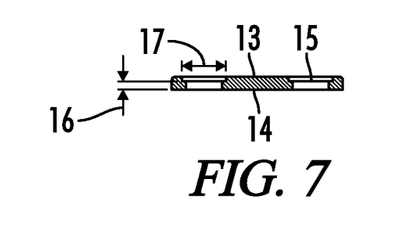
FIG. 7 illustrates a side, cross-sectional view of the plate of FIG. 6, taken along line 7-7 of FIG. 6.
Figure 8:
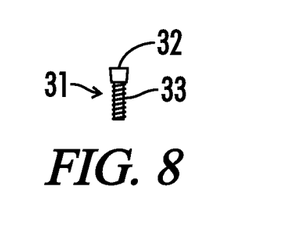
FIG. 8 illustrates a side, elevation view of one embodiment of a fixating screw for use with the plate systems of the present invention.
Figure 9:
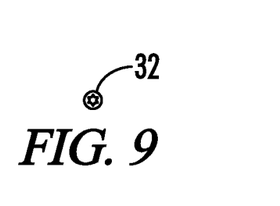
FIG. 9 illustrates a top, plan view of the fixating screw of FIG. 8.
Figure 10:
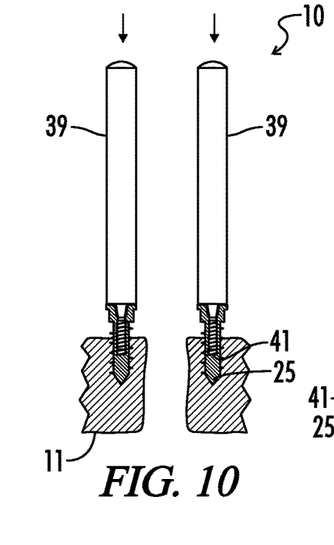
FIG. 10 illustrates a side, cross-sectional view of two distraction screws with expandable heads of one embodiment of a plate system of the present invention being screwed into vertebral bodies using a screw driver.
Figure 11:
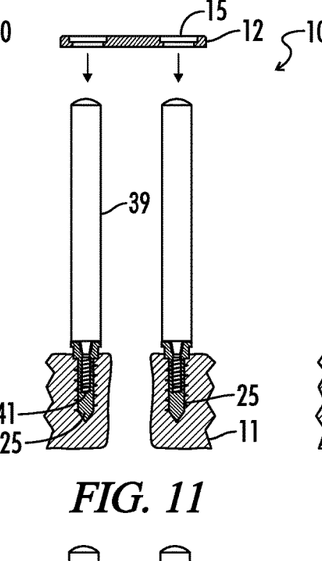
FIG. 11-13 illustrate side, cross-sectional views of a plate of one embodiment of a plate system of the present invention being placed onto two adjacent vertebral bodies.
Figure 12:
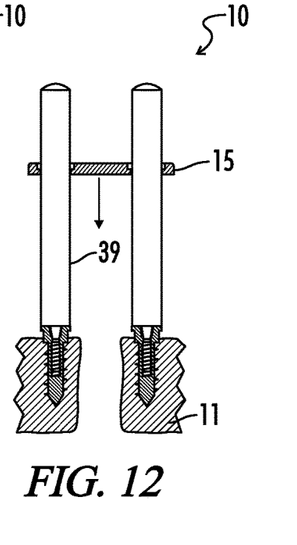
Figure 13:
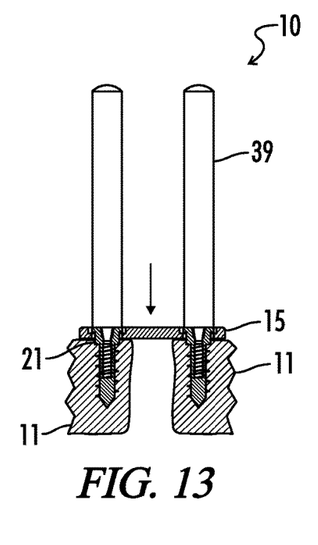
Figure 14:
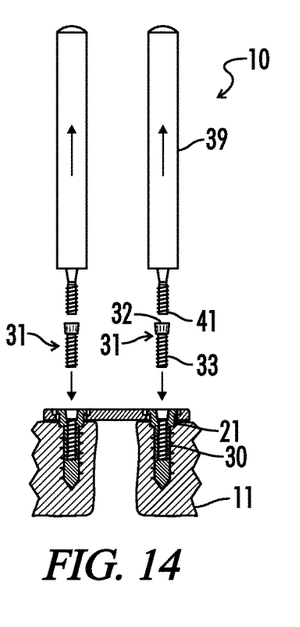
Figure 15:
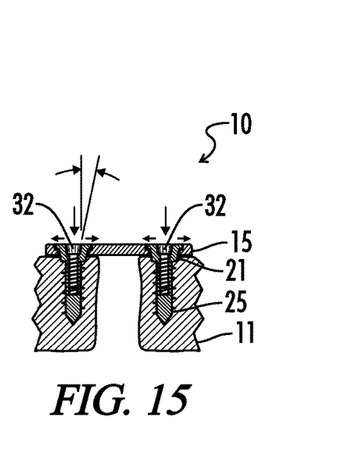
FIG. 15 illustrates a side, cross-sectional view of the fixating screws, distraction screws, plate and vertebral bodies of FIG. 14; the arrows in FIG. 15 show the expandability of the distraction screw heads.
Figure 16:
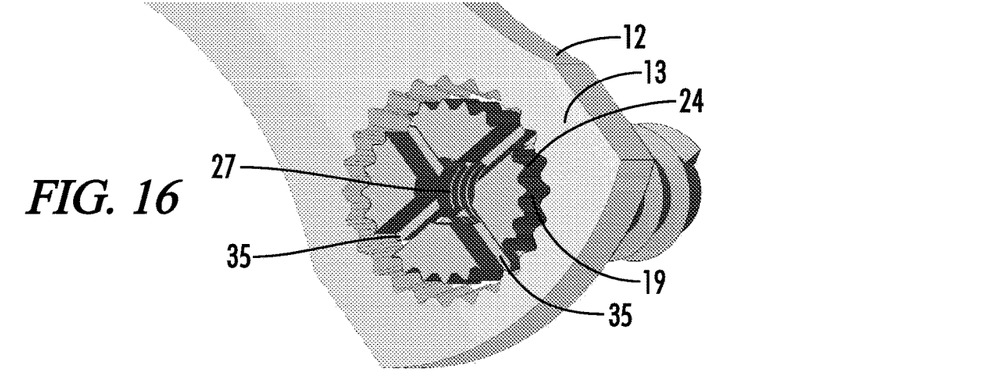
Figure 17:
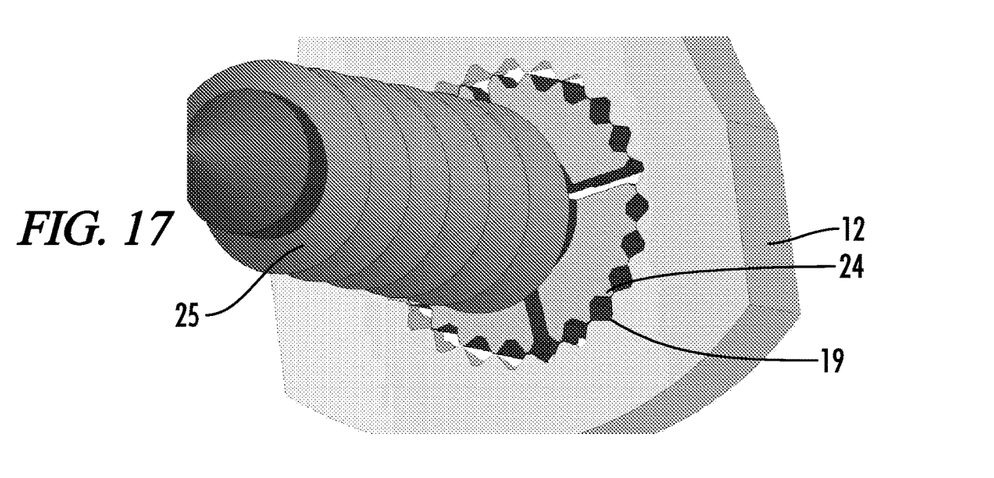
FIG. 17 illustrates a bottom, perspective view of the plate and distraction screw of FIG. 16.
Figure 18:
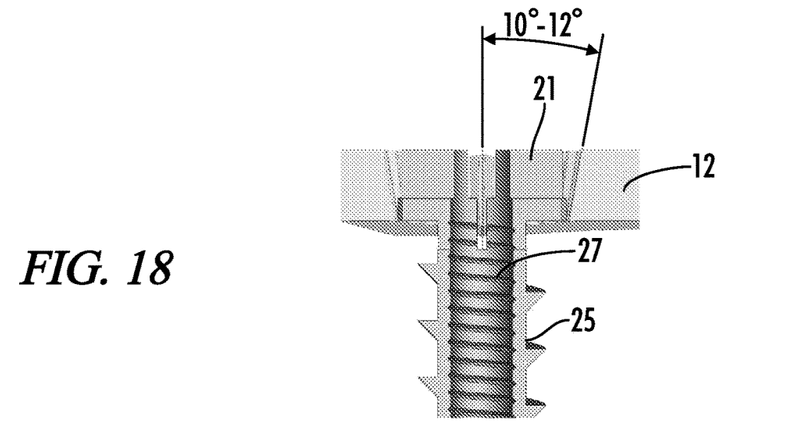
FIG. 18 illustrates a side, cross-sectional view of the plate and distraction screw of FIG. 16.
Figure 19:
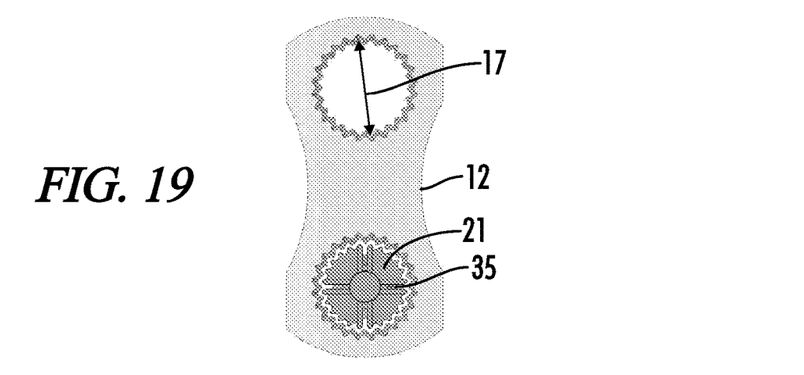
FIG. 19 illustrates a top, plan view of the plate and distraction screw of FIG. 16.
Figure 20:
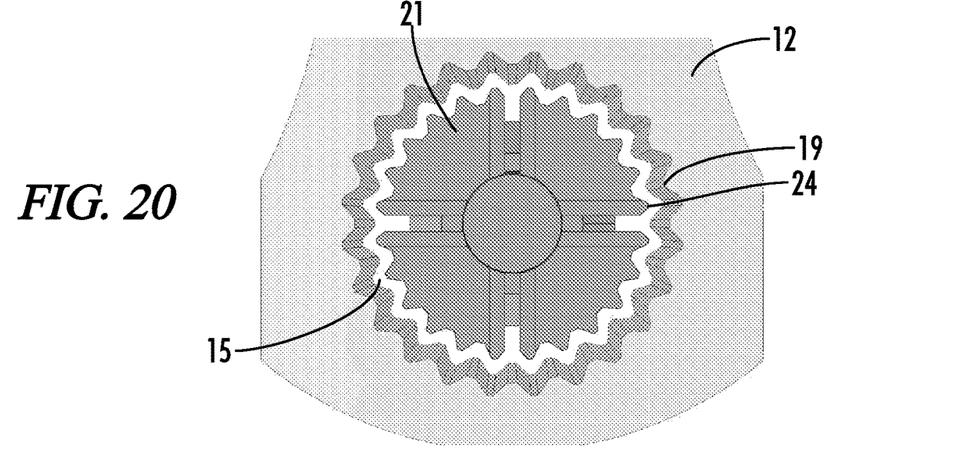
Figure 21:
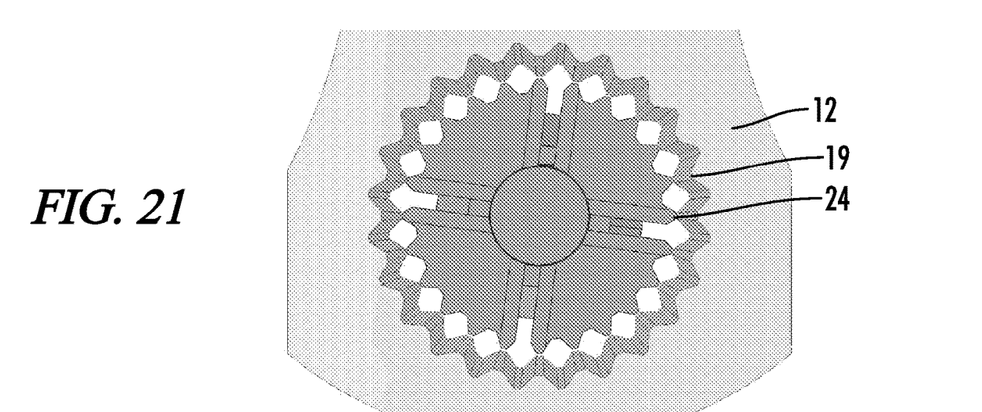
Figure 22:
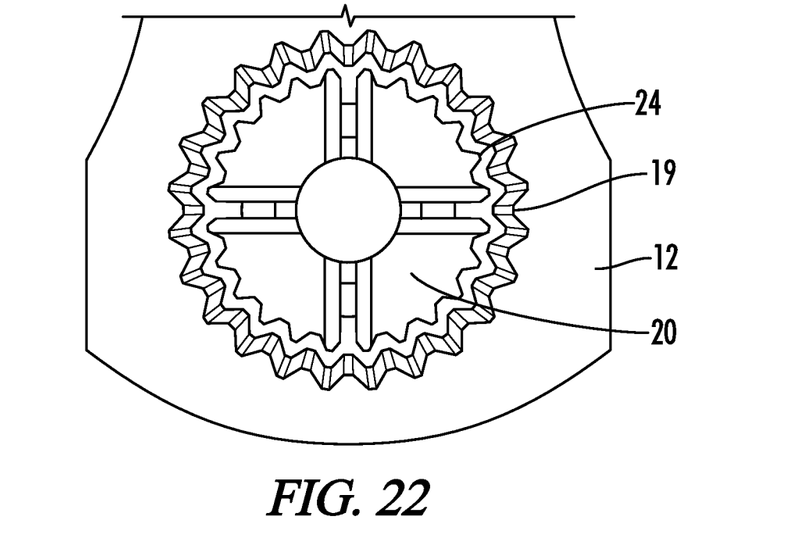
Figure 23:
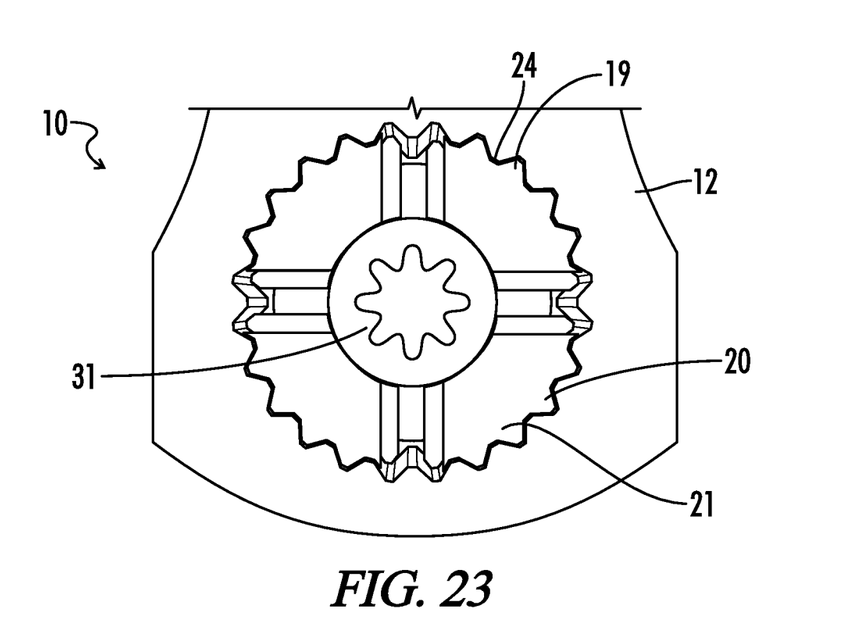

More particularly, with reference to FIGS. 1-23, in some embodiments, the plate system includes:

a) a biocompatible plate 12 comprising a top surface 13, a bottom surface 14 configured to confront a vertebral body 11 and at least two generally circular holes 15, each hole comprising a length 16 extending from the top surface 13 to the bottom surface 14, a diameter 17, and a circumference 18;

b) at least two biocompatible distraction screws 20, each biocompatible distraction screw 20 comprising an expandable head 21, the expandable head 21 generally circular in shape and comprising a circumference 22 and a diameter 23, a shank 25 comprising threads located on an exterior surface of the shank 25, a length 26 extending from the head 21 to the shank 25, and a generally circular bore 27 comprising a top end 28 located in the head 21, a bottom end 29 located in the shank 25, and threads 30, which are spaced about— e.g., lining—the generally circular bore and may extend from the top end 28 to the bottom end 29 of the generally circular bore 27; and c) at least two biocompatible fixating screws 31, each biocompatible fixating screw 31 comprising a head 32 and a shank 33 comprising threads located on an exterior surface of the shank 33, each shank 33 of the biocompatible fixating screw 31 configured to he received in one of the generally circular bores 27 and mate with the threads of the generally circular bore 27. When it is said that the bores 27 are generally circular, it will be understood that the tops 28 of the bores 27 are generally circular, it being understood that the diameter and circumference of the bores 27 may taper/decrease from the bore top end 28 to the bore bottom end 29. Likewise, the generally circular holes 15 may decrease in diameter 17 and circumference 18 from the top plate surface 13 to the bottom plate surface 14 (i.e., along the hole length 16), as best seen in FIG. 18. Preferably, the expandable heads 21 have a radially collapsed state in which the circumference 22 of an expandable head 21 is less than a circumference 18 of a generally circular hole 15 (at a location along the hole length 16) and the diameter 23 of the expandable head 21 is less than a diameter 17 of the generally circular hole 15 (at the same location along the hole length 16), the expandable heads 21 have a radially expanded state in which the circumference 22 of an expandable head 21 expands so that the circumference 22 of the expandable head 21 is substantially equal to a circumference 18 of the generally circular hole 15 (at the same location along the hole length 16) and the diameter 23 of the expandable head 21 expands so that the diameter 23 of the expandable head 21 is substantially equal to a diameter 17 of the generally circular hole 15 (at the same location along the hole length 16), and further wherein insertion of the fixating screws 31 into the distraction screws 20 causes the distraction screw heads 21 to move from the radially collapsed state to the radially expanded state. In other words, the expandable heads 21 have a radially collapsed state in which the circumference 22 and diameter 23 of an expandable head 21 is less than a circumference 18 and diameter 17, respectively, of the generally circular hole 15 (at the location along the hole length 16) that the respective expandable head 21 is located in, and the expandable heads 21 have a radially expanded state in which the circumference 22 and diameter 23 of an expandable head 21 is substantially equal to the circumference 18 and diameter 17 of the generally circular hole 15 (at the same location along the hole length 16) that the respective expandable head 21 is located in. As mentioned above, the generally circular holes 15 may decrease in diameter 17 and circumference 18 from the top plate surface 13 to the bottom plate surface 14 (i.e., along the hole length 16), as best seen in FIG. 18. As seen in FIG. 18, the generally circular holes 15 may be tapered between about 5 and about 15 degrees (more preferably about 10 to about 12 degrees) with respect to the hole length 16—i.e., a line going through the center of the generally circular hole 15. When the fixating screw 31 is screwed into the distraction screw 20, the expandable head 21 of the distraction screw 20 expands to mirror the angle of taper of the generally circular holes 15, which further secures the distraction screws 21 to the plate 12 (i.e., as an additional securing mechanism in addition to the teeth 19 and 24). Preferably, the two or more generally circular holes 15 are the same size, the two or more expandable heads 21 are the same size, and the two or more fixating screws 31 are the same size to allow for interchangeability of the screws 21 and 31 in either plate hole 15.

In a preferred embodiment, as shown in FIGS. 16-23, the plate 12 and expandable heads 21 of the distraction screws 20 comprise mating teeth 19 and 24 that are spaced evenly about the circumferences 18 and 22 of the holes 15 and expandable heads 21, respectively, that lock the expandable heads 21 to the plate 12, upon expansion of the expandable heads 21. It will be understood that when it is said that the plate holes 15 and expandable heads 21 are generally circular, the plate holes 15 and expandable head 21 may include teeth 19 and 24, as shown in FIGS. 16-23. Optionally, the expandable heads 21 include intersecting grooves 35 that traverse the expandable heads 21 to facilitate expansion of the expandable heads 21.

Optionally, the heads 32 of the fixating screws 31 are substantially co-planar with the heads 21 of the distraction screws 20 and the top surface 13 of the plate 12 after screwing the fixating screws 31 into the distraction screws 20. Optionally, the lengths 26 of the distraction screws 20 are greater than the lengths 16 of the generally circular holes 15 so that the distraction screw heads 21 are co-planar with the top surface 13 of the plate 12 after insertion of the distraction screws 20 into the vertebral bodies 11. Optionally, one distraction screw shank 25 is located in a vertebral body 11 of an animal (preferably a human), the other distraction screw shank 25 is located in a different (preferably neighboring) vertebral body 11 of the animal, and the heads 21 of the distraction screws 20 are in the radially expanded state. Optionally, the vertebral bodies 11 are fixed relative to the plate 12 upon screwing the fixating screws 31 into the distraction screws 20 and the resulting expansion of the expandable heads 21. Optionally, each distraction screw 20 is positioned in one of the generally circular holes 15, and each fixating screw 31 is positioned in the generally circular bore 27 of one of the distraction screws 20. Optionally, each generally circular bore 27 is located in the center of an expandable head 21 when the expandable head 21 is in the radially expanded state. Optionally, the system 10 further comprises at least two screw drivers 39, each screw driver 39 comprising a top end comprising a handle 40 and a threaded bottom end 41 configured to mate with the threads 30 of a bore 27 of one of the distraction screws 20.

The present invention also provides a method of fixating a plurality of vertebral bodies 11. In some embodiments, the method includes:

a) providing the plate system 10;

b) using the screw drivers 39 to drive each distraction screw 20 into a vertebral body 11 by placing the threaded bottom end 41 of each screw driver 39 into a distraction screw 20 (preferably into the bore 27 of the distraction screw 20) and rotating the handle 40 of the screw driver 39 (i.e., screwing the distraction screws 20 into the vertebral bodies 11);

c) placing the plate 12 over/onto the vertebral bodies 11 such that each distraction screw 20 is located in a generally circular hole 15;

d) removing the screw drivers 39 from the distraction screws 20 (preferably from generally circular bores 27); and e) radially expanding the expandable heads 21 and fixating the plate 12 to the vertebral bodies 11 by inserting the fixating screws 31 into the bores 27 and rotating the fixating screws 31 relative to the distraction screws 20 (i.e., screwing the fixating screws 31 into the distraction screw bores 27).

Optionally, the method farther includes using the screw drivers 39 to distract the vertebral bodies 11 increase the distance between the vertebral bodies 11) prior to step d). Optionally, the method farther includes adding natural or synthetic bone graft material (e.g., bone graft or bone graft substitute) between the vertebral bodies 11 after distracting the vertebral bodies 11.

Optionally, the distraction screw heads 21, have a circumference of between about 3 mm to about 5 mm in the radially collapsed state and a height of between about 2 mm to about 5 mm, and the threaded shank 25 has a circumference that is smaller than the circumference of the distraction screw head 21 when the distraction screw head 21 is in the radially collapsed and radially expanded states. The fixating screw heads 32 preferably have a circumference that is slightly larger 0.1 to 0.5 mm) than the circumference of the distraction screw heads 21 in the radially collapsed state. Optionally, the fixating screw 31 comprises a slot 44 that has a thickness of between about 0.5 to about 1 mm.

The Embodiments of FIGS. 24-33

Figure 24:
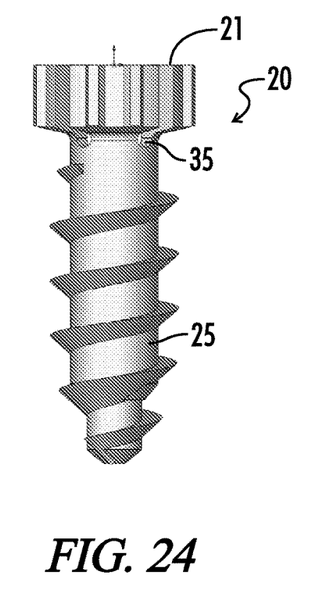
FIG. 24 illustrates a side, elevation view of another embodiment of a distraction screw with an expandable head for use with the plate systems of the present invention.
Figure 25:
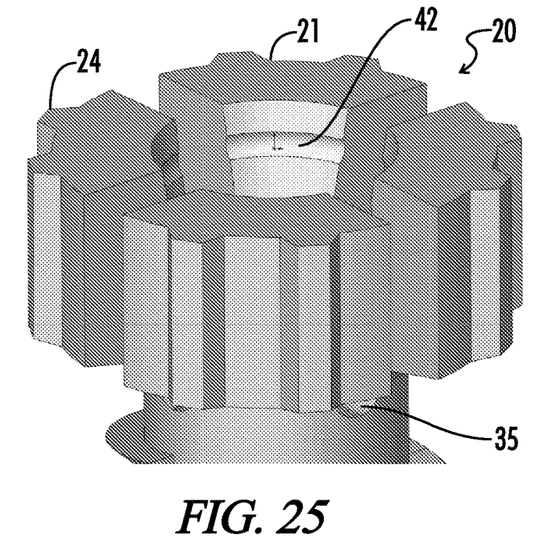
FIG. 25 illustrates a top, perspective view of the distraction screw of FIG. 24.
Figure 26:
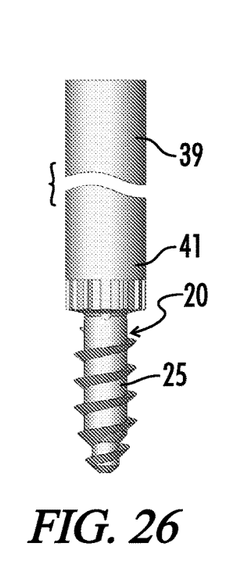
FIG. 26 illustrates a side, elevation view of the distraction screw of FIG. 24 attached to a screw driver.
Figure 27:
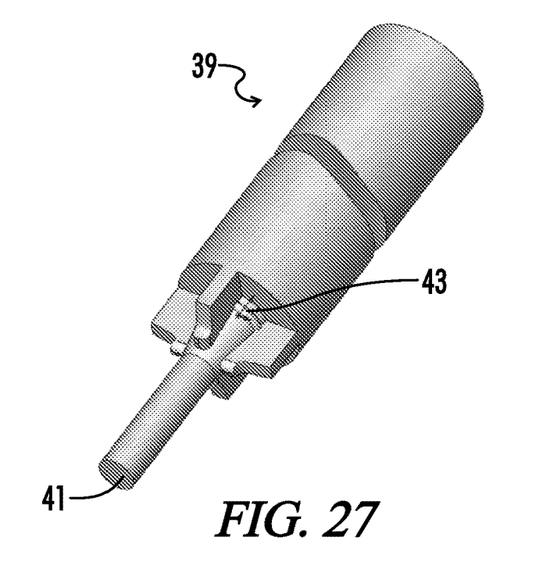
FIG. 27 illustrates, a bottom, perspective view of the screw driver of FIG. 26; the screw driver comprises a flange configured to mate with a groove located in the expandable head of a distraction screw.
Figure 28:
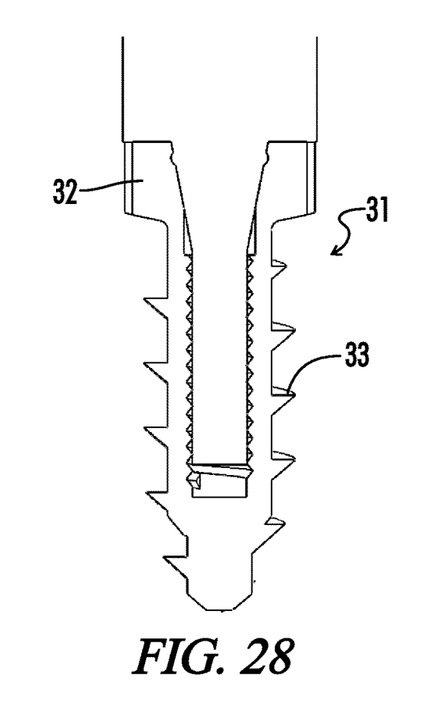
FIG. 28 illustrates a side, cross-sectional view of one embodiment of a fixating screw for use with the plate systems of the present invention.
Figure 29:
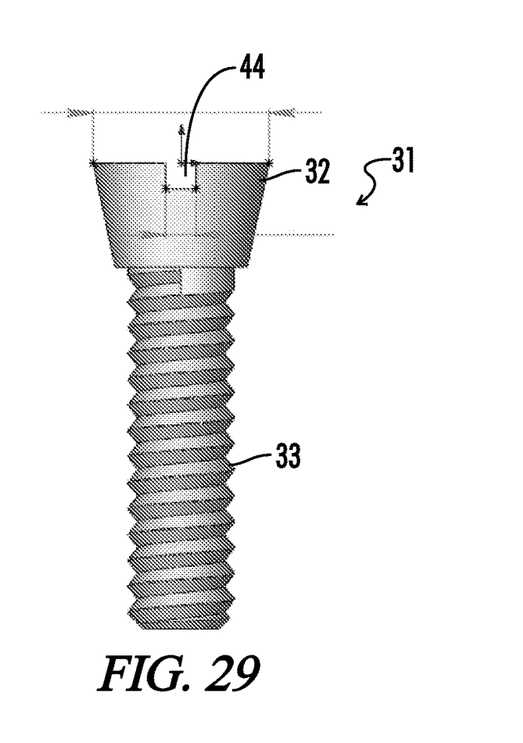
FIG. 29 illustrates a side, elevation view of the fixating screw of FIG. 28.
Figure 30:
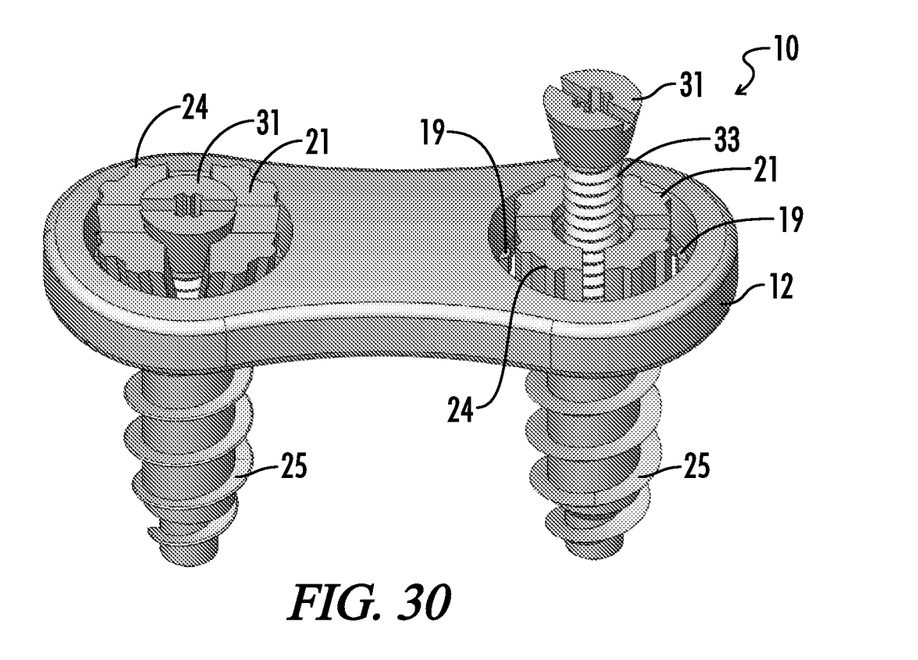
FIG. 30 illustrates a side, elevation view of fixating screws being screwed into distraction screws; the distraction screws are located in a plate and the left fixating screw is almost completely screwed into the left distraction screw, which has moved the expandable head of the left distraction screw to the radially expanded state; the right fixating screw is only partially screwed into the right distraction screw and the head of the right distraction screw is in the radially collapsed state.
Figure 31:
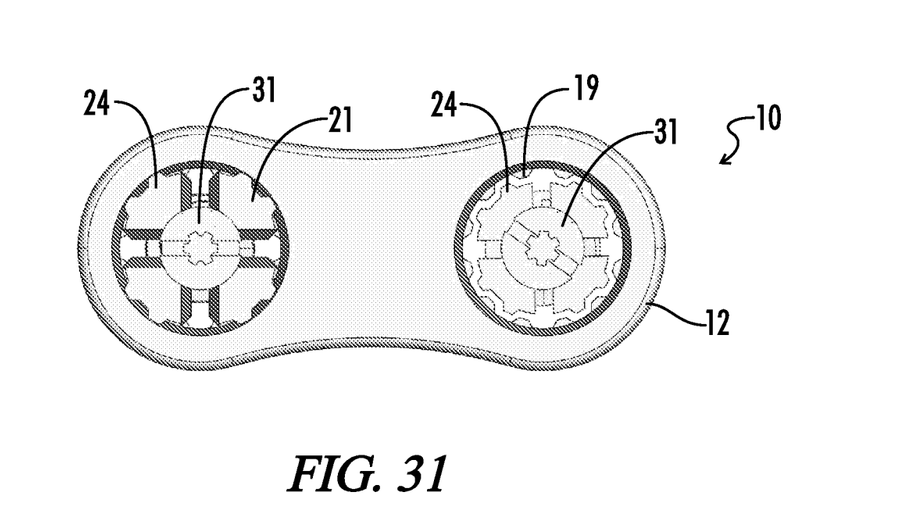
FIG. 31 is a top, plan view of the plate, distraction screws and fixating screws of FIG. 30.
Figure 32:
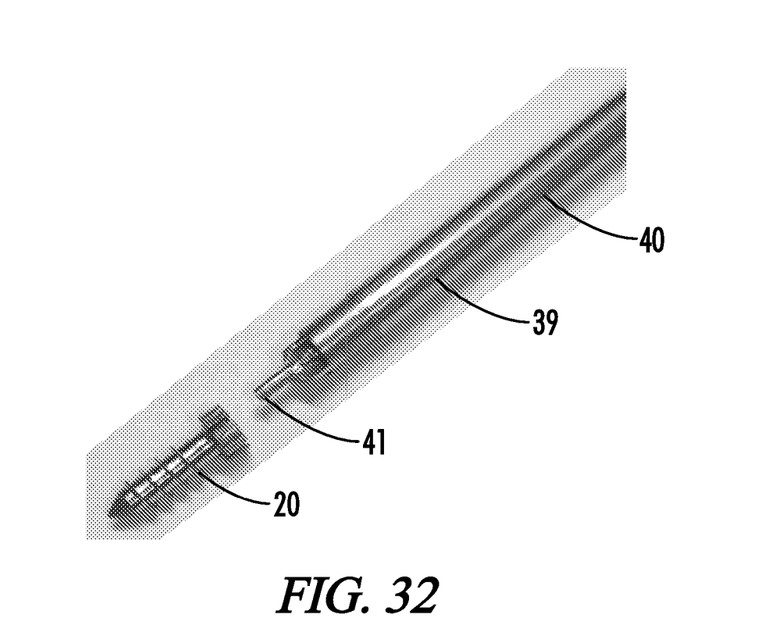
FIG. 32 is a side, elevation view of the screw driver of FIG. 29 and the distraction screw of FIG. 25
Figure 33:
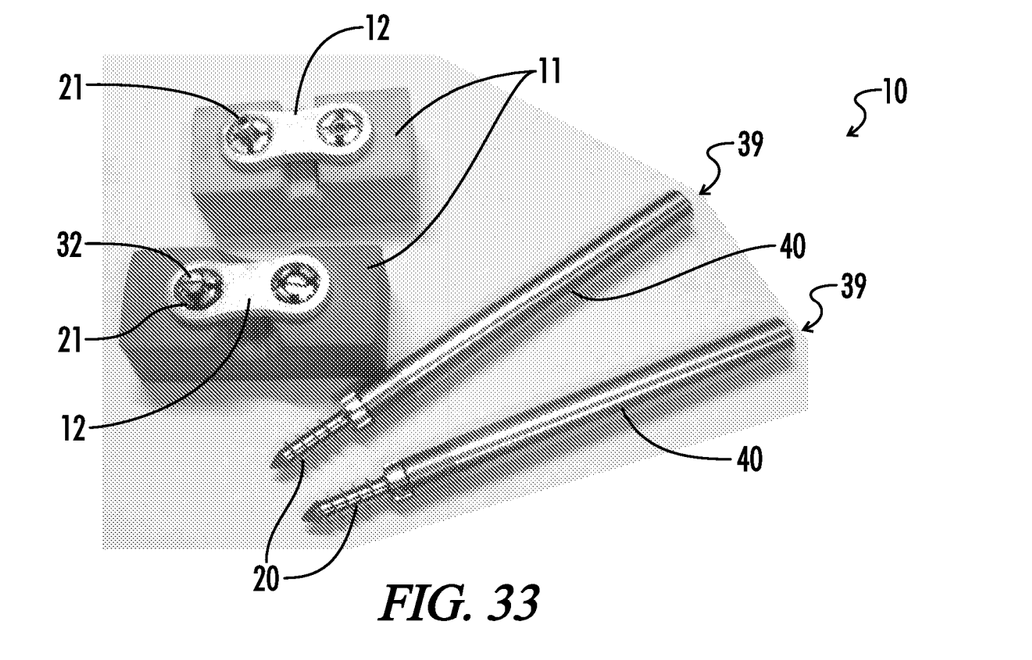
FIG. 33 is a side, elevation view of two plate systems of one embodiment of the present invention attached to a model of adjacent vertebral bodies as well as a side elevation view of two screw drivers wherein each screw driver is attached to a distraction screw.

FIGS. 24-33 illustrate a similar system as illustrated in FIGS. 16-23, except that in the system 10 of FIGS. 24-33, each head 21 of each biocompatible distraction screw 20 further comprises a circumferential groove 42 extending about the circumference of the generally circular bore 27, as best seen in FIG. 25. This circumferential groove 42 functions to mate with a flange 43 located on the screw driver 39, as best seen in FIG. 27, to create a lock and obviate the need fir threads on the bottom end 41 of the screw driver 39. In addition, as best seen in FIGS. 30-31, the teeth 19 of the generally circular plate holes 15 are sunk below the top surface 13 of the plate 12. (As explained in the description of the drawings, FIGS. 30-31 illustrate how insertion of the fixating screw 31 into the distraction screw bores 27 causes the distraction screw heads 21 to radially expand.). FIG. 24 also illustrates how the plurality of grooves 35 of the distraction screw expandable heads 21 may extend into the distraction screw shanks 25.

Having now described the invention in accordance with the requirements of the patent statutes, those skilled, in the art will understand, how to make changes and, modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A plate system for distracting and fixating vertebral bodies comprising
   a) a biocompatible plate comprising a top surface, a bottom surface configured to confront a vertebral body and at least two generally circular holes, each hole comprising a length extending from the top surface to the bottom surface, a diameter, a circumference, and a plurality of teeth spaced evenly about the circumference;
   b) at least two biocompatible distraction screws, each biocompatible distraction screw comprising an expandable head, the expandable head generally circular in shape and comprising a circumference, a diameter and a plurality of teeth spaced evenly about the circumference and configured to engage the teeth of a generally circular hole of the biocompatible plate, a shank comprising threads located on an exterior surface of the shank, a length extending from the head to the shank, and a generally circular bore comprising a top end located in the head, a bottom end located in the shank, and threads spaced about the bore; and
   c) at least two biocompatible fixating screws, each biocompatible fixating screw comprising a head and a shank comprising threads located on an exterior surface of the shank, each shank of each biocompatible fixating screw configured to be received in a generally circular bore and mate with the threads of the generally circular bore, wherein the expandable heads have a radially collapsed state in which the circumferences of the expandable heads are less than the circumferences of the generally circular holes and the diameters of the expandable heads are less than the diameters of the generally circular holes, wherein the expandable heads have a radially expanded state in which the circumferences of the expandable heads are substantially equal to the circumferences of the generally circular holes and the diameters of the expandable heads are substantially equal to the diameters of the generally circular holes, and further wherein insertion of the fixating screws into the distraction screws causes the distraction screw heads to move from the radially collapsed state to the radially expanded state.

2. The plate system of claim 1, wherein the teeth of the generally circular holes of the biocompatible plate are adjacent to the top surface of the biocompatible plate.

3. The plate system of claim 1, wherein each generally circular bore tapers in diameter from the bore top end to the bore bottom end.

4. The plate system of claim 1, wherein each generally circular hole of the biocompatible plate decreases in diameter and circumference from the plate top surface to the plate bottom surface.

5. The plate system of claim 1, wherein each generally circular bore comprises a height extending from top end of the generally circular bore to the bottom end of the generally circular bore and further wherein the threads of each generally circular bore extend substantially the entire height of the generally circular bore.

6. The plate system of claim 1, wherein the heads of the fixating screws are substantially co-planar with the heads of the distraction screws and the top surface of the biocompatible plate.

7. The plate system of claim 6, wherein the fixating screws are located in the generally circular bores.

8. The plate system of claim 6, wherein the distraction screw heads are in the radially expanded state.

9. The plate system of claim 1, wherein the fixating screws are located in the generally circular bores and further wherein the heads of the fixating screws are substantially co-planar with the heads of the distraction screws and below the top surface of the plate.

10. The plate system of claim 1, wherein the lengths of the distraction screws are greater than the lengths of the generally circular holes.

11. The plate system of claim 1, wherein one distraction screw shank is located in a vertebral body of an animal, the other distraction screw shank is located in another vertebral body of the animal, and the heads of the distraction screws are in the radially expanded state.

12. The plate system of claim 11, wherein the vertebral bodies are fixed relative to the plate.

13. The plate system of claim 1, wherein each distraction screw is positioned in one of the generally circular holes, and each fixating screw is positioned in the bore of one of the distraction screws.

14. The plate system of claim 1, wherein each expandable head comprises a plurality of grooves.

15. The plate system of claim 14, wherein the plurality of grooves traverse the expandable head.

16. The plate system of claim 15, wherein the plurality of grooves on each distraction screw extend into the shank of the distraction screw.

17. The plate system of claim 1, wherein each generally circular bore is located in the center of an expandable head when the expandable head is in the radially expanded state.

18. The plate system of claim 1, wherein the system further comprises at least two screw drivers, each screw driver comprising a top end comprising a handle and a threaded bottom end configured to mate with the threads of a generally circular bore of one of the distraction screws.

19. The plate system of claim 1, wherein each generally circular bore of each biocompatible distraction screw further comprises a circumference and further wherein each head of each biocompatible distraction screw further comprises a circumferential groove extending about the circumference.

20. The plate system of claim 19, wherein the system further comprises at least two screw drivers, each screw driver comprising a top end comprising a handle, a bottom end configured to be inserted in a generally circular bore, and a flange configured to mate with a circumferential groove of a biocompatible distraction screw.

21. A method of fixating a plurality of vertebral bodies comprising:
 a) providing the plate system of claim 1 and at least two screw drivers, each screw driver comprising a top end comprising a handle, a bottom end;
 b) using the screw drivers to drive the distraction screws into the plurality of vertebral bodies by placing the bottom end of each screw driver into a generally circular bore of the distraction screw and rotating the handle of the screw driver;
 c) placing the plate over the vertebral bodies such that each distraction screw is located in a generally circular hole;
 d) removing the screw drivers from the generally circular bores; and
 e) radially expanding the expandable heads and fixating the plate to the vertebral bodies by inserting the fixating screws into the generally circular bores and rotating the fixating screws relative to the distraction screws.

22. The method of claim 21, further comprising using the screw drivers to distract the vertebral bodies prior to step d).

23. The method of claim 21 further comprising adding bone graft material between the vertebral bodies after distracting the vertebral bodies.

* * * * *